United States Patent [19]

Howard

[11] Patent Number: 5,026,946

[45] Date of Patent: Jun. 25, 1991

[54] HOMOGENEOUS PARTIAL OXIDATION OF A METHANE-CONTAINING PARAFFINIC HYDROCARBON

[75] Inventor: Mark J. Howard, Feltham, England

[73] Assignee: The British Petroleum Company p.l.c., London, England

[21] Appl. No.: 224,166

[22] Filed: Jul. 26, 1988

[30] Foreign Application Priority Data

Aug. 5, 1987 [GB] United Kingdom ............... 8718488

[51] Int. Cl.$^5$ .............................................. C07C 2/00
[52] U.S. Cl. ................................. 585/500; 585/700; 585/943; 585/910; 585/911
[58] Field of Search ............ 585/500, 700, 943, 910, 585/911

[56] References Cited

U.S. PATENT DOCUMENTS

| | | | |
|---|---|---|---|
| 1,978,621 | 10/1934 | Burke | 568/474 |
| 2,672,488 | 3/1954 | Jones | 585/911 |
| 2,679,542 | 5/1954 | Dorsey | 585/910 |
| 2,679,543 | 5/1954 | Dorsey | 585/910 |
| 2,713,601 | 7/1955 | Bills | 585/910 |
| 2,726,276 | 12/1955 | Dorsey | 585/910 |
| 2,905,731 | 9/1959 | Seep | 585/911 |
| 3,236,905 | 2/1966 | Otsuka et al. | 585/910 |

FOREIGN PATENT DOCUMENTS

| | | |
|---|---|---|
| 0178853 | 4/1986 | European Pat. Off. . |
| 85/00164 | 1/1985 | PCT Int'l Appl. . |
| 0818395 | 8/1959 | United Kingdom . |

Primary Examiner—Patrick P. Garvin
Assistant Examiner—E. D. Irunski
Attorney, Agent, or Firm—Brooks Haidt Haffner & Delahunty

[57] ABSTRACT

A $C_2$ and higher hydrocarbon product including ethylene is produced from a methane-containing gaseous paraffinic hydrocarbon feedstock by a process comprising heating the feedstock admixed with oxygen in an amount of at least 5% mol under elevated pressure in a pre-heating zone to a temperature sufficient to cause spontaneous reaction, the pre-heating and mixing being effected in a manner such that (i) substantial oxygen consumption is avoided, and (ii) a "flash-back" of the reaction to form a diffusion flame at the point of gaseous mixing is prevented, and thereafter in a reaction zone allowing the feedstock mixture to spontaneously react.

12 Claims, 1 Drawing Sheet

HOMOGENEOUS PARTIAL OXIDATION OF A METHANE-CONTAINING PARAFFINIC HYDROCARBON

The present invention relates in general to the homogeneous partial oxidation of a methane-containing paraffinic hydrocarbon feedstock and in particular to operation of the process in a manner whereby $C_2$ and higher hydrocarbons, for example ethylene, are produced.

Homogeneous reaction of pre-mixed methane/oxygen mixtures is known in the art for the production of higher hydrocarbons at pressures up to about 4 bar. See for example SRI Report No. 16, 1966, "Acetylene" by H. C. Ries. The hydrocarbons formed are mainly acetylene. Significant amounts of ethylene are also observed in some devices, for example a spouted bed reactor as disclosed in our European patent application publication No. 0178853. The co-products principally comprise carbon monoxide, hydrogen and water, together with low levels of carbon dioxide.

Similar mixtures can also be produced at higher pressures using burner type devices having a non-premixed reaction zone. This has been disclosed in our published European application No. 904585.

Partial oxidation of methane in premixed methane/oxygen mixtures at high pressure, for example greater than 20 bar, is known for the production of partial oxygenates, principally comprising methanol and formaldehyde. Thus, U.S. Pat. No. 4,618,732 discloses a process for converting natural gas containing methane to methanol, comprising:

thoroughly and intimately mixing natural gas with gaseous air or oxygen to achieve substantially complete homogeneity of these gases;

feeding the resulting gas mixture to an inert reactor under elevated pressure, said reactor having an internal surface surrounding a zone in which said gases react, said surface being made of a material selected from the group consisting of glass, non-reactive plastics, non-reactive waxes and non-reactive salts; and reacting said gases in said reaction zone at an elevated temperature in the absence in said reaction zone of any added material which measurably affects the rate of selectivity of the reaction or the yield of product.

The co-products of this type of reaction are principally carbon dioxide and water.

Formation of methanol and formaledhyde is known to be favoured by low reaction temperatures (400°–500° C.), high pressures (greater than 20 bar) and low oxygen concentrations (less than or equal to 5% mol), preferably outside flammable limits. This restricts conversion to low levels for premixed mixtures, in which increase of oxygen content causes loss of partial oxygenates and possible 'flash backs' through the feed to the point of gas mixing. Higher conversions can be achieved more safely by adding oxygen incrementally throughout the reaction zone (staged oxygen addition), although partial oxygenate selectivity still falls rapidly with conversion.

Finally, K. Asami et al report in J. Chem. Soc., Chem. Commun. 1987, pp 1287–1288 that methane can be non-catalytically oxidised in a flow-type tubular reactor into which quartz tubes are inserted to minimise direct contact of the reactant gases with the metal surface to give ethane and ethylene at pressures up to 1.6 MPa in the temperature range 650° to 800° C. The gas mixture contained 84% mol nitrogen diluent, and the reaction would appear to be a gradual isothermal oxidation. The maximum conversion of methane achieved was 10.2%, which is far too low for economic commercial operation. A desirable objective would be to increase the methane conversion and selectivity to ethylene of the non-catalytic oxidation of methane.

During our studies on the production of partial oxygenates we have surprisingly found that high methane conversions and ethane/ethylene selectivities can be achieved without diluent at high pressure by preheating a methane-containing gaseous paraffinic hydrocarbon and oxygen under controlled conditions to a point at which spontaneous reaction occurs.

Accordingly, the present invention provides a process for the production of a $C_2$ and higher hydrocarbons product including ethylene from a methane-containing gaseous paraffinic hydrocarbon feedstock which process comprises heating under elevated pressure in a pre-heating zone a mixture of the feedstock and oxygen in an amount of at least 5% mol to a temperature sufficient to cause spontaneous reaction, the pre-heating and mixing being effected in a manner such that (i) substantial oxygen consumption is avoided, and (ii) a "flash-back" of the reaction to form a diffusion flame at the point of gaseous mixing is prevented, and thereafter in a reaction zone allowing the feedstock mixture to spontaneous react.

An advantage of the process of the invention as hereinbefore described is that it can be operated in a manner which does not produce significant quantities of acetylene, which is difficult to quench. A quench step can be avoided. The product of the process is $C_2$ and higher hydrocarbons comprising a substantial proportion of ethylene. In addition there is formed substantial amounts of carbon monoxide and hydrogen, which are themselves valuable products.

The methane-containing gaseous paraffinic hydrocarbon feedstock may be substantially pure methane or it may be methane in combination with one or more other gaseous paraffinic hydrocarbons, for example ethane, propane or butane. A particularly preferred feedstock is natural gas, the composition of which depends upon its origin, but generally principally comprises methane, with varying proportions of ethane, propane and butane. Natural gas containing sulphur is preferably desulphurised before use as a feedstock. The methane-containing feedstock may also contain inert gases, for example nitrogen. Other cofeeds, for example hydrogen, carbon monoxide, carbon dioxide or steam, may also be used if so desired.

The oxygen used in the performance of the invention may be molecular oxygen, air or oxygen-enriched air. It is preferred to use oxygen either in pure form or containing minor proportions of inert gases, for example nitrogen. Preferably oxygen is present in an amount of greater than 10% mol.

Pre-heating in a manner such that (i) substantial oxygen consumption is avoided, and (ii) a "flash-back" of the reaction to form a diffusion flame at the point of gaseous mixing is prevented may suitably be accomplished by mixing the methane-containing gaseous paraffinic hydrocarbon feedstock and oxygen at ambient temperature, and then rapidly heating to the spontaneous reaction temperature in a region wherein the gas velocity exceeds the propagation velocity of the reaction. Alternatively, in a particularly preferred embodiment of the invention mixing and preheating may be accomplished simultaneously by the incremental addition of oxygen to hydrocarbon gas flowing through an externally heated region. This region may be empty, but the velocity of the gas flowing therethrough may be sufficiently high to prevent reaction. Alternatively, it may contain a packed bed of inert material. The packed bed may suitably be comprised of a granular or powdered material capable of preventing flame propagation and slower oxidation reactions occurring to a significant extent. A wide range of materials may suitably perform this function, for example fused alumina granules which may either be clean or washed with potassium chloride solution or zirconia powder, suitably of a particle size in the range from 400 to 850 microns. Other materials which may be treated with substances such as potassium chloride or lead oxide.

It is thought, though we do not wish to be bound to any theory, that the aforesaid materials function chemically to, by surface reaction, destroy chemical species that propagate or chain-branch oxidation reactions and physically by acting as a heat sink to prevent the progress of a flame front.

The elevated pressure at which the mixture of gases is heated is preferably greater than 20 bar. The temperature sufficient to cause spontaneous reaction of the gaseous mixture will to some extent depend on the composition of the mixture but will generally be at least 400° C.

The gaseous mixture at, or above, the point of spontaneous ignition is passed to the reaction zone wherein it is allowed to spontaneously ignite. A spontaneous homogeneous reaction occurs which consumes the available oxygen. During the reaction the gas temperature rises rapidly to a value dependent upon the initial oxygen content (typically greater than 800° C.). The product selectivity to $C_{2+}$ hydrocarbons may exceed 40% C mol, whilst the hydrogen/carbon monoxide ratio generally exceeds 1.0. Conversion generally exceeds 15%, and is limited only by the reaction temperatures that can be tolerated by the apparatus and the effectiveness of the inhibition during preheat. Maximum preheat levels are desirable. The reaction zone is preferably maintained under adiabatic conditions.

It will be apparent from the foregoing that the reaction zone should be fabricated in a material capable of withstanding high temperatures, for example up to 1200° C.

The product resulting from operation of the process of the invention may be separated into its individual components or may be reacted together in a subsequent synthesis reactor to produce, for example, carbonylated products.

The invention will now be further illustrated by the following Examples with reference to the accompanying Drawings.

Figure 1:
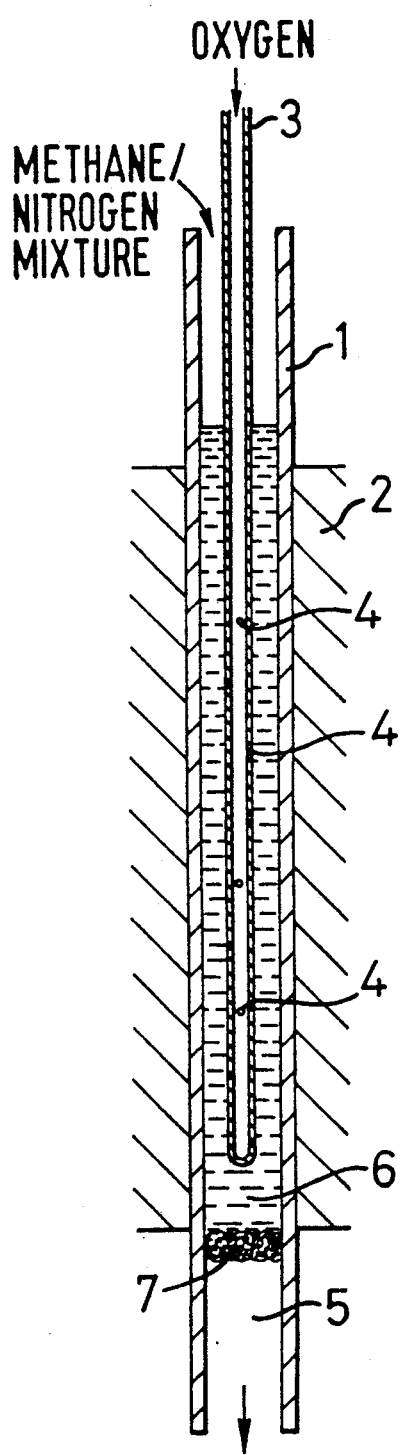
FIG. 1 is a schematic representation of one form of apparatus useful in the performance of the invention.
Figure 2:
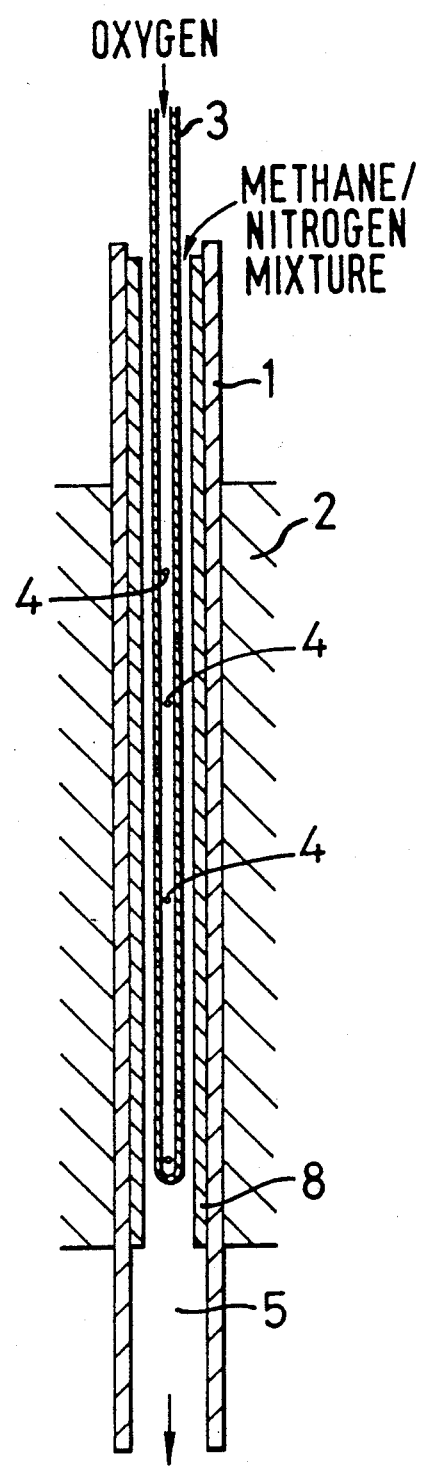
FIG. 2 is a schematic representation of a second form of apparatus useful in the performance of the invention.

With reference to the FIGS. 1 is a 9 mm internal diameter stainless steel tube, 2 is a mixing and pre-heating zone enclosed within a furnace (not shown), 3 is an oxygen injector consisting of a tube closed at the end within the tube 1 and having 10 holes (0.1 mm) 4 evenly spaced along the tube and 5 is a reaction zone. With specific reference to FIG. 1, 6 is a packing of fused alumina granules and 7 is a glass wool plug. With specific reference to FIG. 2, 8 is a stainless steel tube liner.

EXAMPLES 1 to 5

With reference to FIG. 1, methane/nitrogen mixtures were fed to the tube 1 and passed through a packed bed approximately 30 cm long of fused alumina granules 6 heated by an external furnace (not shown). The portion of the tube 1 within the furnace constituted the mixing and pre-heating zone 2. Oxygen was fed through the oxygen injector 3 and passed through the holes 4 into the methane/nitrogen mixture flowing through the tube 1, thereby mixing in a staged manner with the methane/nitrogen mixture and simultaneously being progressively heated. On leaving the zone 2, the pre-mixed and pre-heated gas was allowed to spontaneously ignite in the reaction zone 5. The glass wool plug 7 was present to minimise the escape of fused alumina granules.

Results at 20 to 40 bar pressure are shown in Table 1.

EXAMPLE 6

The procedure of Examples 1 to 5 was employed using the apparatus of FIG. 2 instead of that of FIG. 1 at 40 bar pressure. The difference between the apparatus of FIG. 1 and the apparatus of FIG. 2 is that instead of the packing 6, the tube 1 is fitted with a stainless steel tube liner 8 of 6.2 mm internal diameter to reduce the residence time in the mixing and pre-heating zone 2. In all other respects apart from the absence of the glass wool plug 7, which is rendered redundant by the absence of the packing, the apparatus is identical to that of FIG. 1.

The results are given in Table 1.

The oxygen content, and therefore conversion in the experiments reported, is limited by the tolerance of the reactor to high temperatures.

EXAMPLES 7 TO 9

The procedure of Examples 1 to 5 was repeated using, instead of the stainless steel tube 1, a Hastalloy reactor and an increased oxygen content of the gaseous mixture.

The reactant compositions, the reaction conditions and the results are given in Table 2.

The adiabatic reaction temperature at higher oxygen content exceeds the temperature rating of even the Hastalloy reactor (about 800° C.) and some external cooling was necessary. Higher conversions and $C_{2+}$ selectivities are expected under the preferred adiabatic reaction conditions.

TABLE 1

Production of Higher Hydrocarbons from Methane at High Pressure

| EX-AMPLE | PRESS (bar) | FLOW (nlmin$^{-1}$) | PRE-HEAT (°C.) | *FEED COMP (% vol) | | | METHANE CONV. (%) | PRODUCT SELECTIVITY (% C mol) | | | | | | | | H$_2$/CO |
|---|---|---|---|---|---|---|---|---|---|---|---|---|---|---|---|---|
| | | | | CH$_4$ | O$_2$ | N$_2$ | | CO | CO$_2$ | C$_2$H$_6$ | C$_2$H$_4$ | C$_3$ | C$_4$ | C$_6$H$_6$ | C$_{2+}$ | |
| 1 | 40 | 5.5 | 460 | 85.5 | 12.9 | 1.6 | 17.8 | 56.9 | 6.3 | 15.3 | 13.2 | 4.4 | 0.4 | 3.5 | 36.8 | 1.01 |
| 2** | 40 | 5.8 | 470 | 85.6 | 11.4 | 3.0 | 16.2 | 52.8 | 5.6 | 13.6 | 17.9 | 5.4 | 0.4 | 4.3 | 41.6 | 1.01 |
| 3 | 30 | 5.8 | 480 | 86.0 | 12.4 | 1.6 | 19.0 | 57.0 | 5.8 | 11.4 | 15.3 | 3.9 | 0.4 | 6.2 | 37.2 | 1.35 |
| 4 | 30 | 5.7 | 480 | 86.8 | 11.6 | 1.6 | 16.5 | 54.4 | 5.5 | 10.1 | 19.0 | 6.3 | 0.2 | 4.5 | 40.1 | 1.11 |
| 5 | 20 | 5.7 | 516 | 86.7 | 11.7 | 1.6 | 16.0 | 55.3 | 5.6 | 7.5 | 22.2 | 6.3 | 0.8 | 2.3 | 39.1 | 1.01 |

TABLE 1-continued

Production of Higher Hydrocarbons from Methane at High Pressure

| EX-AMPLE | PRESS (bar) | FLOW (nlmin$^{-1}$) | PRE-HEAT (°C.) | *FEED COMP (% vol) CH$_4$ | O$_2$ | N$_2$ | METHANE CONV. (%) | PRODUCT SELECTIVITY (% C mol) CO | CO$_2$ | C$_2$H$_6$ | C$_2$H$_4$ | C$_3$ | C$_4$ | C$_6$H$_6$ | C$_2$+ | H$_2$/CO |
|---|---|---|---|---|---|---|---|---|---|---|---|---|---|---|---|---|
| 6# | 40 | 5.6 | 460 | 85.0 | 12.0 | 3.0 | 15.8 | 47.7 | 12.3 | 12.0 | 19.2 | 5.8 | 0.8 | 2.2 | 40.0 | 1.00 |

*Derived feed.
**Fused alumina granules washed with KCl solution.
Stainless steel liner only.

TABLE 2

| EX-AMPLE | PRES-SURE (bar) | FLOW (nlmin$^{-1}$) | PRE-HEAT (°C.) | *FEED COMP (% vol) CH$_4$ | O$_2$ | N$_2$ | METHANE CONV. (%) | PRODUCT SELECTIVITY (% C mol) CO | CO$_2$ | C$_2$H$_6$ | C$_2$H$_4$ | C$_3$ | C$_4$ | C$_6$H$_6$ | C$_2$+ | H$_2$/CO |
|---|---|---|---|---|---|---|---|---|---|---|---|---|---|---|---|---|
| 7 (230) | 40 | 5.5 | 480 | 82.8 | 13.6 | 3.6 | 18.9 | 43.8 | 15.6 | 16.9 | 13.6 | 4.4 | 0.4 | 3.8 | 39.1 | 1.24 |
| 8 (239) | 30 | 5.7 | 485 | 81.4 | 15.0 | 3.6 | 21.7 | 54.3 | 11.0 | 14.4 | 11.7 | 2.5 | 0.3 | 5.1 | 34.0 | 1.24 |
| 9 (236) | 20 | 4.1 | 545 | 75.5 | 19.5 | 5.0 | 27.0 | 56.3 | 9.5 | 9.9 | 14.7 | 1.8 | 0.2 | 5.4 | 32.0 | — |

*Derived feed.
Clean Fused Alumina Granules

I claim:

1. A process for the production of a C$_2$ and higher hydrocarbon product including ethylene from a methane-containing gaseous paraffinic hydrocarbon feedstock which process comprises heating under elevated pressure in a pre-heating zone a mixture of the feedstock and oxygen in an amount of at least 5% mol to a temperature sufficient to cause spontaneous reaction, the pre-heating and mixing being effected in a manner such that (i) substantial oxygen consumption is avoided, and (ii) a "flash-back" of the reaction to form a diffusion flame at the point of gaseous mixing is prevented, and thereafter in a reaction zone allowing the feedstock mixture to spontaneously react under essentially adiabatic conditions.

2. A process according to claim 1 wherein in the preheating zone the methane-containing gaseous paraffinic hydrocarbon feedstock and oxygen are mixed at ambient temperature and then rapidly heated to the spontaneous reaction temperature in region wherein the gas velocity exceeds the propagation velocity of the reaction.

3. A process according to claim 1 wherein mixing and preheating are accomplished simultaneously by the incremental addition of oxygen to the methane-containing paraffinic hydrocarbon feedstock flowing through an externally heated region.

4. A process according to claim 3 wherein the externally heated region is unpacked and the velocity of the gas flowing therethrough is sufficiently high to prevent reaction.

5. A process according to claim 3 wherein the externally heated region contains a packed bed of inert material.

6. A process according to claim 5 wherein the inert material is comprised of a granular or powdered material capable of preventing flame propagation and slower oxidation reactions occuring to a significant extent.

7. A process according to claim 1 wherein the elevated pressure is greater than 20 bar.

8. A process according to claim 1 wherein the temperature sufficient to cause spontaneous reaction is at least 400° C.

9. A process according to claim 1 wherein oxygen is present in an amount greater than 10 mol %.

10. A process according to claim 1 wherein the feedstock is methane.

11. A process according to claim 10 wherein the methane is combined with one or more other gaseous paraffinic hydrocarbons.

12. A process according to claim 1 wherein the feedstock is natural gas.

* * * * *

UNITED STATES PATENT AND TRADEMARK OFFICE
CERTIFICATE OF CORRECTION

| | | |
|---|---|---|
| PATENT NO. | : | 5,026,946 |
| DATED | : | June 25, 1991 |
| INVENTOR(S) | : | MARK J. HOWARD |

It is certified that error appears in the above-identified patent and that said Letters Patent is hereby corrected as shown below:

Col. 3, l. 13, after "materials" and before "which", insert --which may be employed include fused silica, magnesia, and the like,--

Signed and Sealed this

First Day of December, 1992

Attest:

DOUGLAS B. COMER

Attesting Officer

Acting Commissioner of Patents and Trademarks